United States Patent
Hara et al.

(10) Patent No.: US 10,004,720 B2
(45) Date of Patent: Jun. 26, 2018

(54) AGENT FOR PREVENTING AND/OR TREATING OPHTHALMOLOGIC DISEASES

(71) Applicant: MITSUBISHI TANABE PHARMA CORPORATION, Osaka (JP)

(72) Inventors: Hideaki Hara, Gifu (JP); Masamitsu Shimazawa, Gifu (JP); Tomomi Masuda, Gifu (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days. days.

(21) Appl. No.: 15/512,200

(22) PCT Filed: Mar. 19, 2015

(86) PCT No.: PCT/JP2015/058164
§ 371 (c)(1),
(2) Date: Mar. 17, 2017

(87) PCT Pub. No.: WO2016/042812
PCT Pub. Date: Mar. 24, 2016

(65) Prior Publication Data
US 2017/0273949 A1 Sep. 28, 2017

(30) Foreign Application Priority Data
Sep. 19, 2014 (JP) .................................. 2014-191106

(51) Int. Cl.
*A61K 31/4152* (2006.01)
*A61K 9/00* (2006.01)
*C07D 231/26* (2006.01)
*A61K 31/4155* (2006.01)

(52) U.S. Cl.
CPC ........ *A61K 31/4152* (2013.01); *A61K 9/0048* (2013.01); *A61K 31/4155* (2013.01); *C07D 231/26* (2013.01)

(58) Field of Classification Search
CPC ................................................ A61K 31/4152
See application file for complete search history.

(56) References Cited

FOREIGN PATENT DOCUMENTS

| EP | 0 208 874 | 1/1987 |
| EP | 0 633 025 | 1/1995 |
| EP | 1 297 849 | 4/2003 |
| JP | 5-31523 | 5/1993 |
| JP | 5-35128 | 5/1993 |
| JP | 7-25765 | 1/1995 |
| JP | 2003-252760 | 9/2003 |
| JP | 2003252760 | * 9/2003 |
| WO | 02/00260 | 3/2002 |

OTHER PUBLICATIONS

Masuda et al, Apr. 2014, ARVO Annual Meeting Abstract, p. 1-3.*
Dombrow, Jan./Feb. 2011, Retinal Physician, p. 1-13.*
English machine translation of JP2003252760, Sep. 2003, p. 1-7.*
International Search Report dated Apr. 21, 2015 in International (PCT) Application No. PCT/JP2015/058164.
International Preliminary Report on Patentability dated Mar. 30, 2017 in International (PCT) Application No. PCT/JP2015/058164.
Saint-Geniez et al., "An essential role for RPE-derived soluble VEGF in the maintenance of the choriocapillaris", PNAS, vol. 106, No. 44, 2009, pp. 18751-18756.
Nishijima et al., "Vascular Endothelial Growth Factor-A is a Survival Factor for Retinal Neurons and a Critical Neuroprotectant during the Adaptive Response to Ischemic Injury" The American Journal of Pathology, vol. 171, No. 1, 2007, pp. 53-67.
Shimazaki et al., "Edaravone-Loaded Liposome Eyedrops Protect against Light-Induced Retinal Damage in Mice", Investigative Ophthalmology & Visual Science, vol. 52, No. 10, 2011, pp. 7289-7297.
Masuda et al., "Mouse Oyobi Marmoset no Laser Yuhatsu Myakurakumalcu Kekkan Shinsei nl Taisuru Edaravone no Yokusei Sayo", Dai 34 Kai Japanese Society for Ocular Pharmacology Program•Koen Shorokushu, 2014, p. 35, with English translation.
Masuda et. al., Edaravone, a free radical scavenger, inhibits laser-induced choroidal neovascularization in mice by reducing the oxidative stress., ARVO 2014 Annual Meeting Abstracts, [online], 2014, Program No. 621, Poster Board No. B0148.
Shimazawa et al., "N-methyl-N-nitrosourea Yuhatsu Mouse Shisaibo Hensei nl Taisuru Edaravone no Sayo", Dai 30 Kai Japanese Society for Ocular Pharmacology Program Koen Shorokushu, 2010, p. 38, with English translation.
Hironaka et al., "Tengan shita Edaravone Funyu Liposome no Momaku Shogai nl Taisuru Hogo Koka", Drug Deliv Syst, 2011, 26-3, p. 295, with English translation.
Nagai et al., "Momaku Hikari Shogai Model nl Taisuru Keikyomaku Drug Delivery Device no Momaku Hogo Koka", Journal of Japanese Ophthalmological Society, 2012, vol. 116, special extra issue, p. 306, with English translation.

* cited by examiner

*Primary Examiner* — Rebecca L Anderson
*Assistant Examiner* — Karen Cheng
(74) *Attorney, Agent, or Firm* — Wenderoth, Lind & Ponack, L.L.P.

(57) ABSTRACT

It is an object of the present invention to provide a novel medicament for preventing and/or treating ophthalmologic diseases caused by ocular angiogenesis. According to the present invention, provided is a medicament for preventing and/or treating ophthalmologic diseases caused by ocular angiogenesis, which comprises, as an active ingredient, a pyrazolone derivative such as 3-methyl-1-phenyl-2-pyrazolin-5-one, or a physiologically acceptable salt thereof, or a hydrate thereof or a solvate thereof.

13 Claims, 1 Drawing Sheet

[Figure 1]
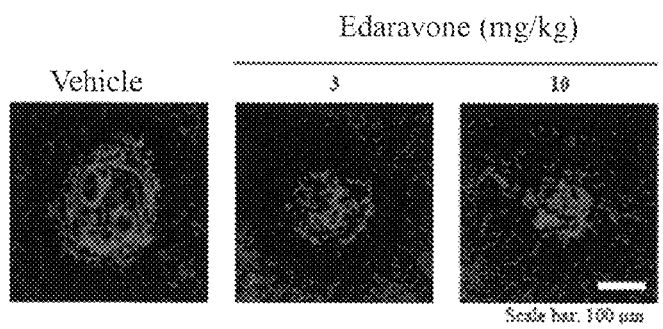
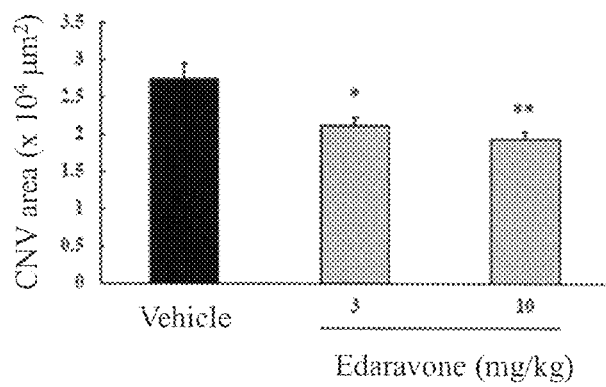
[Figure 2]
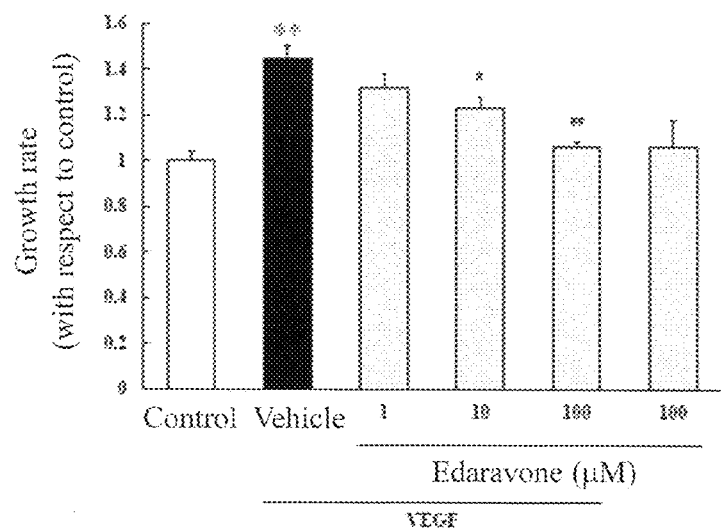

AGENT FOR PREVENTING AND/OR TREATING OPHTHALMOLOGIC DISEASES

TECHNICAL FIELD

The present invention relates to a medicament for preventing and/or treating ophthalmologic diseases caused by ocular angiogenesis, which comprises, as an active ingredient, a pyrazolone derivative or a physiologically acceptable salt thereof, or a hydrate thereof or a solvate thereof.

BACKGROUND ART

It has been known that angiogenesis has a great influence on wound healing and progression of many diseases. As ophthalmologic diseases with which angiogenesis is associated, retinopathy of prematurity, diabetic retinopathy, wet age-related macular degeneration, neovascular glaucoma, neovascular maculopathy, and the like have been known. Moreover, corneal neovascularization caused by various stimuli given to cornea or invasion therein has also been known. In these diseases, a control mechanism-lacked angiogenesis has occurred. A vascular endothelial growth factor (VEGF) is associated with such angiogenesis. Examples of a known anti-VEGF drug may include Bevacizumab as an anti-VEGF antibody, Sorafenib, Sunitinib, Pegaptanib sodium, Ranibizumab, Aflibercept, and VEGF-Trap EYE. Medicaments that target VEGF have been widely used in clinical sites for the treatment of eye diseases such as age-related macular degeneration, branch retinal vein occlusion, central retinal vein occlusion, diabetic maculopathy, diabetic retinopathy, and neovascular glaucoma. However, VEGF has various actions, such as the maintenance of homeostasis of normal retinochoroidal vessels (see, for example, Non Patent Literature 1) and action as a nutritional factor for retinal neurons (see, for example, Non Patent Literature 2).

On the other hand, with regard to a pyrazolone derivative represented by the following formula (I):

[Formula 1]

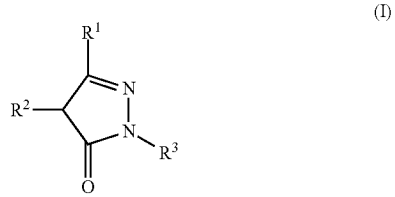

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl, or $C_{1-3}$ hydroxyalkyl, or $R^1$ and $R^2$ are combined with each other to represent $C_{3-5}$ alkylene, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, a halogen atom, trifluoromethyl, carboxyl, cyano, a hydroxyl group, nitro, amino, and acetamide, it has been known that this pyrazolone derivative has, as intended use of a medicament, brain function-normalizing action (Patent Literature 1), lipid peroxide generation-inhibiting action (Patent Literature 2), eye cloudiness-inhibiting action (Patent Literature 3), action to inhibit retinal neurodegeneration (Patent Literature 4), and action to inhibit progression of atrophic age-related macular degeneration (Non Patent Literature 3). However, these publications neither suggest nor teach the effectiveness of this compound as a therapeutic agent or a preventive agent for ophthalmologic diseases caused by ocular angiogenesis.

PRIOR ART LITERATURES

Patent Literatures

Patent Literature 1: JP Patent Publication (Kokoku) No. 5-31523 B (1993)
Patent Literature 2: JP Patent Publication (Kokoku) No. 5-35128 B (1993)
Patent Literature 3: JP Patent Publication (Kokai) No. 7-25765 A (1995)
Patent Literature 4: WO2002/00260

Non Patent Literatures

Non Patent Literature 1: Proc. Natl. Acad. Sci., 2009, 106: 18751-18756
Non Patent Literature 2: Am. J. Patho., 2007, 171: 53-67
Non Patent Literature 3: Investigative Ophthalmology & Visual Science, 2011, vol. 52, No. 10: 7289-7297

DISCLOSURE OF INVENTION

Object to be Solved by the Invention

As described above, since VEGF has various actions, such as the maintenance of homeostasis of normal retinochoroidal vessels and action as a nutritional factor for retinal neurons, it cannot be denied that inhibition of such VEGF for a long period of time may have adverse effects on ocular tissues. Thus, the development of a therapeutic method that targets molecules other than VEGF is one of the objects.

It is an object of the present invention to provide a novel medicament for preventing and/or treating ophthalmologic diseases caused by ocular angiogenesis.

Means for Solving the Object

For the purpose of achieving the aforementioned object, the present inventors have conducted studies regarding the action of a pyrazolone derivative represented by the formula (I) on ocular angiogenesis. As a result, ocular angiogenesis could be inhibited by administration of the above-described pyrazolone derivative, and thus, the inventors have found that ophthalmologic diseases caused by ocular angiogenesis can be prevented and/or treated, thereby completing the present invention.

The present invention provides the following invention.
(1) A medicament for preventing and/or treating ophthalmologic diseases caused by ocular angiogenesis, which comprises, as an active ingredient, a pyrazolone derivative represented by the following formula (I), or a physiologically acceptable salt thereof, or a hydrate thereof or a solvate thereof:

[Formula 2]

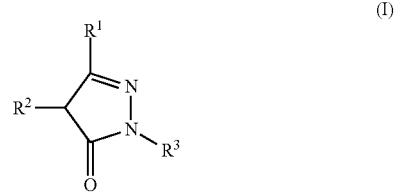

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl, or $C_{1-3}$ hydroxyalkyl, or $R^1$ and $R^2$ are combined with each other to represent $C_{3-5}$ alkylene, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, a halogen atom, trifluoromethyl, carboxyl, cyano, a hydroxyl group, nitro, amino, and acetamide.

(2) The medicament according to (1), wherein the pyrazolone derivative represented by the formula (I) is 3-methyl-1-phenyl-2-pyrazolin-5-one.

(3) The medicament according to (1) or (2), wherein the ophthalmologic diseases caused by ocular angiogenesis are ophthalmologic diseases caused by angiogenesis occurring in cornea, choroid or retina.

(4) The medicament according to any one of (1) to (3), wherein the ophthalmologic disease caused by ocular angiogenesis is retinopathy of prematurity, diabetic retinopathy, corneal neovascularization, wet age-related macular degeneration, neovascular glaucoma, choroidal neovascularization, neovascular maculopathy, branch retinal vein occlusion, central retinal vein occlusion, branch retinal artery occlusion, central retinal artery occlusion, or diabetic maculopathy.

(5) A medicament for preventing and/or treating wet age-related macular degeneration or neovascular maculopathy, which comprises, as an active ingredient, 3-methyl-1-phenyl-2-pyrazolin-5-one.

(6) An agent for inhibition of ocular angiogenesis, which comprises, as an active ingredient, a pyrazolone derivative represented by the following formula (I), or a physiologically acceptable salt thereof, or a hydrate thereof or a solvate thereof:

[Formula 3]

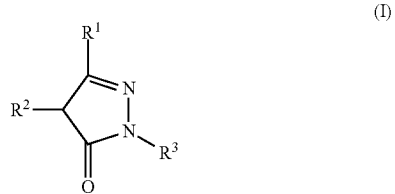

(I)

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl, or $C_{1-3}$ hydroxyalkyl, or $R^1$ and $R^2$ are combined with each other to represent $C_{3-5}$ alkylene, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, a halogen atom, trifluoromethyl, carboxyl, cyano, a hydroxyl group, nitro, amino, and acetamide.

(7) The agent for inhibition of ocular angiogenesis according to (6), wherein the pyrazolone derivative represented by the formula (I) is 3-methyl-1-phenyl-2-pyrazolin-5-one.

(8) The agent for inhibition of ocular angiogenesis according to (6) or (7), wherein the ocular angiogenesis is angiogenesis occurring in cornea, choroid or retina.

(9) The agent for inhibition of ocular angiogenesis according to any one of (6) to (8), wherein the ocular angiogenesis is inhibited by suppressing cell growth induced by a vascular endothelial growth factor (VEGF).

(10) A method for preventing and/or treating ophthalmologic diseases caused by ocular angiogenesis, which comprises a step of administering, to mammals including humans, an effective amount of a pyrazolone derivative represented by the aforementioned formula (I), or a physiologically acceptable salt thereof, or a hydrate thereof or a solvate thereof:

(11) The method according to (10), wherein the pyrazolone derivative represented by the formula (I) is 3-methyl-1-phenyl-2-pyrazolin-5-one.

(12) The method according to (10) or (11), wherein the ophthalmologic diseases caused by ocular angiogenesis are ophthalmologic diseases caused by angiogenesis occurring in cornea, choroid or retina.

(13) The method according to any one of (10) to (12), wherein the ophthalmologic disease caused by ocular angiogenesis is retinopathy of prematurity, diabetic retinopathy, corneal neovascularization, wet age-related macular degeneration, neovascular glaucoma, choroidal neovascularization, neovascular maculopathy, branch retinal vein occlusion, central retinal vein occlusion, branch retinal artery occlusion, central retinal artery occlusion, or diabetic maculopathy.

(14) A method for preventing and/or treating wet age-related macular degeneration or neovascular maculopathy, which comprises a step of administering an effective amount of 3-methyl-1-phenyl-2-pyrazolin-5-one to mammals including humans.

(15) A method for inhibiting ocular angiogenesis, which comprises a step of administering, to mammals including humans, an effective amount of a pyrazolone derivative represented by the aforementioned formula (I), or a physiologically acceptable salt thereof, or a hydrate thereof or a solvate thereof:

(16) The method according to (15), wherein the pyrazolone derivative represented by the formula (I) is 3-methyl-1-phenyl-2-pyrazolin-5-one.

(17) The method according to (15) or (16), wherein the ocular angiogenesis is angiogenesis occurring in cornea, choroid or retina.

(18) The method according to any one of (15) to (17), wherein the ocular angiogenesis is inhibited by suppressing cell growth induced by a vascular endothelial growth factor (VEGF).

(19) Use of a pyrazolone derivative represented by the aforementioned formula (I), or a physiologically acceptable salt thereof, or a hydrate thereof or a solvate thereof, for producing a medicament for preventing and/or treating ophthalmologic diseases caused by ocular angiogenesis:

(20) The use according to (19), wherein the pyrazolone derivative represented by the formula (I) is 3-methyl-1-phenyl-2-pyrazolin-5-one.

(21) The use according to (19) or (20), wherein the ophthalmologic diseases caused by ocular angiogenesis are ophthalmologic diseases caused by angiogenesis occurring in cornea, choroid or retina.

(22) The use according to any one of (19) to (21), wherein the ophthalmologic disease caused by ocular angiogenesis is retinopathy of prematurity, diabetic retinopathy, corneal neovascularization, wet age-related macular degeneration, neovascular glaucoma, choroidal neovascularization, neovascular maculopathy, branch retinal vein occlusion, central retinal vein occlusion, branch retinal artery occlusion, central retinal artery occlusion, or diabetic maculopathy.

(23) Use of 3-methyl-1-phenyl-2-pyrazolin-5-one for producing a medicament for preventing and/or treating wet age-related macular degeneration or neovascular maculopathy.

(24) Use of a pyrazolone derivative represented by the aforementioned formula (I), or a physiologically acceptable salt thereof, or a hydrate thereof or a solvate thereof, for producing an agent for inhibition of ocular angiogenesis:

(25) The use according to (24), wherein the pyrazolone derivative represented by the formula (I) is 3-methyl-1-phenyl-2-pyrazolin-5-one.

(26) The use according to (24) or (25), wherein the ocular angiogenesis is angiogenesis occurring in cornea, choroid or retina.

(27) The use according to any one of (24) to (26), wherein the ocular angiogenesis is inhibited by suppressing cell growth induced by a vascular endothelial growth factor (VEGF).

Advantageous Effects of Invention

The medicament according to the present invention can effectively inhibit ocular angiogenesis, and is effective for the prevention and/or treatment of ophthalmologic diseases caused by ocular angiogenesis.

BRIEF DESCRIPTION OF DRAWINGS

FIG. 1 shows the effects obtained by intravenous administration of edaravone on CNV formation in mice. The data indicate an average±SEM (n=7 to 9). With respect to the vehicle administration group, *P<0.05, and **P<0.01 (Dunnett's test).

FIG. 2 shows the effects of edaravone on VEGF-induced cell growth. The data indicate an average±SEM (n=6). With respect to the control group, P<0.01 (Student's t test), and with respect to the vehicle administration group, P<0.01 (Dunnett's test).

BEST MODE FOR CARRYING OUT INVENTION

The medicament for preventing and/or treating ophthalmologic diseases caused by ocular angiogenesis according to the present invention and the agent for inhibition of ocular angiogenesis according to the present invention (hereinafter collectively referred to as "the medicament of the present invention," at times) comprise, as an active ingredient, a pyrazolone derivative represented by the formula (I), or a physiologically acceptable salt thereof, or a hydrate thereof or a solvate thereof.

The compound represented by the formula (I) may also have a structure represented by the following formula (I') or (I"), as a result of tautomerism. In the present description, the formula (I) shows one tautomer, for convenience of explanation. However, the presence of the following tautomers is obvious to a person skilled in the art. As an active ingredient of the medicament of the present invention, the compound represented by the following formula (I') or (I"), a physiologically acceptable salt thereof, or a hydrate thereof or a solvate thereof may be used.

[Formula 4]

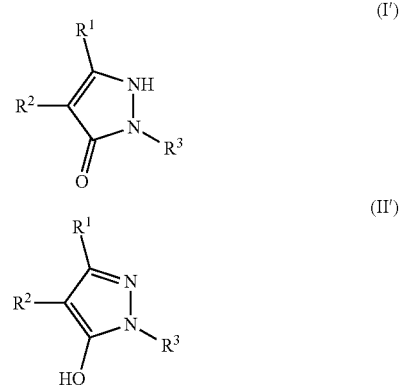

In the formula (I), the aryl group in the definition of $R^1$ may be either a monocyclic or polycyclic aryl group. Examples of the aryl group may include a phenyl group, a naphthyl group, and phenyl groups substituted with substituent such as alkyl groups (for example, methyl group and a butyl group), alkoxy groups (for example, methoxy group and a butoxy group), halogen atoms (for example, a chlorine atom) or a hydroxyl group. The same applies to an aryl portion in other substituents having such an aryl portion (e.g., an aryloxy group, etc.).

The $C_{1-5}$ alkyl group in the definition of $R^1$, $R^2$ and $R^3$ may be either a linear or branched alkyl group. Examples of the $C_{1-5}$ alkyl group may include a methyl group, an ethyl group, a propyl group, an isopropyl group, a butyl group, an isobutyl group, a sec-butyl group, a tert-butyl group, and a pentyl group. The same applies to an alkyl portion in other substituents having such an alkyl portion (e.g., an alkoxycarbonylalkyl group, etc.).

Examples of the $C_{3-6}$ (total carbon number) alkoxycarbonylalkyl group in the definition of $R^1$ may include a methoxycarbonylmethyl group, an ethoxycarbonylmethyl group, a propoxycarbonylmethyl group, a methoxycarbonylethyl group, and a methoxycarbonylpropyl group.

Examples of the $C_{3-5}$ alkylene group in the definition of $R^1$ and $R^2$ may include a trimethylene group, a tetramethylene group, a pentamethylene group, a methyltrimethylene group, an ethyltrimethylene group, a dimethyltrimethylene group, and a methyltetramethylene group.

Examples of the aryloxy group in the definition of $R^2$ may include a p-methylphenoxy group, a p-methoxyphenoxy group, a p-chlorophenoxy group, and a p-hydroxyphenoxy group. Examples of the arylmercapto group may include a phenylmercapto group, a p-methylphenylmercapto group, a p-methoxyphenylmercapto group, a p-chlorophenylmercapto group, and a p-hydroxyphenylmercapto group.

Examples of the $C_{1-3}$ hydroxyalkyl group in the definition of $R^2$ and $R^3$ may include a hydroxymethyl group, a 2-hydroxyethyl group, and a 3-hydroxypropyl group. Examples of the $C_{5-7}$ cycloalkyl group in the definition of $R^3$ may include a cyclopentyl group, cyclohexyl group, and a cycloheptyl group.

Examples of the $C_{1-5}$ alkoxy group as a substituent for the phenyl group in the definition of $R^3$ may include a methoxy group, an ethoxy group, a propoxy group, an isopropoxy group, a butoxy group, and a pentyloxy group. Examples of the $C_{2-5}$ (total carbon number) alkoxycarbonyl group may include a methoxycarbonyl group, an ethoxycarbonyl group, a propoxycarbonyl group, and a butoxycarbonyl group.

Examples of the $C_{1-3}$ alkylmercapto group may include a methylmercapto group, an ethylmercapto group, and a propylmercapto group. Examples of the $C_{1-4}$ alkylamino group may include a methylamino group, an ethylamino group, a propylamino group, and a butylamino group. Examples of the $C_{2-8}$ (total carbon number) dialkylamino group may include a dimethylamino group, a diethylamino group, a dipropylamino group, and a dibutylamino group.

Examples of the compound (I) that is preferably used as an active ingredient of the medicament of the present invention may include the following compounds.
3-methyl-1-phenyl-2-pyrazolin-5-one;
3-methyl-1-(2-methylphenyl)-2-pyrazolin-5-one;
3-methyl-1-(3-methylphenyl)-2-pyrazolin-5-one;
3-methyl-1-(4-methylphenyl)-2-pyrazolin-5-one;
3-methyl-1-(3,4-dimethylphenyl)-2-pyrazolin-5-one;
1-(4-ethylphenyl)-3-methyl-2-pyrazolin-5-one;
3-methyl-1-(4-propylphenyl)-2-pyrazolin-5-one;
1-(4-butylphenyl)-3-methyl-2-pyrazolin-5-one;
1-(3-trifluoromethylphenyl)-3-methyl-2-pyrazolin-5-one;
1-(4-trifluoromethylphenyl)-3-methyl-2-pyrazolin-5-one;
1-(2-methoxyphenyl)-3-methyl-2-pyrazolin-5-one;
1-(3-methoxyphenyl)-3-methyl-2-pyrazolin-5-one;
1-(4-methoxyphenyl)-3-methyl-2-pyrazolin-5-one;
1-(3,4-dimethoxyphenyl)-3-methyl-2-pyrazolin-5-one;
1-(4-ethoxyphenyl)-3-methyl-2-pyrazolin-5-one;
3-methyl-1-(4-propoxyphenyl)-2-pyrazolin-5-one;
1-(4-butoxyphenyl)-3-methyl-2-pyrazolin-5-one;
1-(2-chlorophenyl)-3-methyl-2-pyrazolin-5-one;
1-(3-chlorophenyl)-3-methyl-2-pyrazolin-5-one;
1-(4-chlorophenyl)-3-methyl-2-pyrazolin-5-one;
1-(3,4-dichlorophenyl)-3-methyl-2-pyrazolin-5-one;
1-(4-bromophenyl)-3-methyl-2-pyrazolin-5-one;
1-(4-fluorophenyl)-3-methyl-2-pyrazolin-5-one;
1-(3-chloro-4-methylphenyl)-3-methyl-2-pyrazolin-5-one;
1-(3-methylmercaptophenyl)-3-methyl-2-pyrazolin-5-one;
1-(4-methylmercaptophenyl)-3-methyl-2-pyrazolin-5-one;
4-(3-methyl-5-oxo-2-pyrazoline-1-yl) benzoic acid;
1-(4-ethoxycarbonylphenyl)-3-methyl-2-pyrazolin-5-one;
1-(4-nitrophenyl)-3-methyl-2-pyrazolin-5-one;
3-ethyl-1-phenyl-2-pyrazolin-5-one;
1-phenyl-3-propyl-2-pyrazolin-5-one;
1,3-diphenyl-2-pyrazolin-5-one;
3-phenyl-1-(p-tolyl)-2-pyrazolin-5-one;
1-(4-methoxyphenyl)-3-phenyl-2-pyrazolin-5-one;
1-(4-chlorophenyl)-3-phenyl-2-pyrazolin-5-one;
3,4-dimethyl-1-phenyl-2-pyrazolin-5-one;
4-isobutyl-3-methyl-1-phenyl-2-pyrazolin-5-one;
4-(2-hydroxyethyl)-3-methyl-1-phenyl-2-pyrazolin-5-one;
3-methyl-4-phenoxy-1-phenyl-2-pyrazolin-5-one;
3-methyl-4-phenylmercapto-1-phenyl-2-pyrazolin-5-one;
3,3',4,5,6,7-hexahydro-2-phenyl-2H-indazol-3-one;
3-(ethoxycarbonylmethyl)-1-phenyl-2-pyrazolin-5-one;
1-phenyl-2-pyrazolin-5-one;
3-methyl-2-pyrazolin-5-one;
1,3-dimethyl-2-pyrazolin-5-one;
1-ethyl-3-methyl-2-pyrazolin-5-one;
1-butyl-3-methyl-2-pyrazolin-5-one;
1-(2-hydroxyethyl)-3-methyl-2-pyrazolin-5-one;
1-cyclohexyl-3-methyl-2-pyrazolin-5-one;
1-benzyl-3-methyl-2-pyrazolin-5-one;
1-(α-naphthyl)-3-methyl-2-pyrazolin-5-one;
1-methyl-3-phenyl-2-pyrazolin-5-one;
3-methyl-1-(4-methylphenyl)-2-pyrazolin-5-one;
1-(4-butylphenyl)-3-methyl-2-pyrazolin-5-one;
1-(4-methoxyphenyl)-3-methyl-2-pyrazolin-5-one;
1-(4-butoxyphenyl)-3-methyl-2-pyrazolin-5-one;
1-(4-chlorophenyl)-3-methyl-2-pyrazolin-5-one;
1-(4-hydroxyphenyl)-3-methyl-2-pyrazolin-5-one;
1-(3,4-dihydroxyphenyl)-3-methyl-2-pyrazolin-5-one;
1-(2-hydroxyphenyl)-3-methyl-2-pyrazolin-5-one;
1-(3-hydroxyphenyl)-3-methyl-2-pyrazolin-5-one;
1-(4-hydroxyphenyl)-3-methyl-2-pyrazolin-5-one;
1-(3,4-hydroxyphenyl)-3-methyl-2-pyrazolin-5-one;
1-(4-hydroxyphenyl)-3-phenyl-2-pyrazolin-5-one;
1-(4-hydroxymethylphenyl)-3-methyl-2-pyrazolin-5-one;
1-(4-aminophenyl)-3-methyl-2-pyrazolin-5-one;
1-(4-methylaminophenyl)-3-methyl-2-pyrazolin-5-one;
1-(4-ethylaminophenyl)-3-methyl-2-pyrazolin-5-one;
1-(4-butylaminophenyl)-3-methyl-2-pyrazolin-5-one;
1-(4-dimethylaminophenyl)-3-methyl-2-pyrazolin-5-one;
1-(acetamidophenyl)-3-methyl-2-pyrazolin-5-one; and
1-(4-cyanophenyl)-3-methyl-2-pyrazolin-5-one.

As an active ingredient of the medicament of the present invention, not only a free-form compound represented by the formula (I), but a physiologically acceptable salt thereof may also be used. Examples of the physiologically acceptable salt may include: mineral acid salts such as hydrochloride, sulfate, hydrobromide, and phosphate; organic acid salts such as methanesulfonate, p-toluenesulfonate, acetate, oxalate, citrate, malate, and fumarate; alkaline metal salts such as sodium salts and potassium salts; alkaline-earth metal salts such as magnesium salts; and amine salts such as ammonia, ethanolamine, and 2-amino-2-methyl-1-propanol.

In addition to these salts, the type of the salt is not particularly limited, as long as it is physiologically acceptable.

The compounds represented by the formula (I) are all known compounds, and these compounds can be easily synthetized by a person skilled in the art according to the method described in JP Patent Publication (Kokoku) No. 5-31523 B (1993) or the like.

The dose of the medicament of the present invention is not particularly limited. When the compound represented by the formula (I) is used as an active ingredient of the medicament, in general, in the case of oral administration, the weight of the compound represented by the formula (I) is 0.1 to 100 mg/kg of body weight per day, and in the case of parenteral administration, it is 0.1 to 100 mg/kg of body weight per day. The above-described dose is preferably administered once, or divided over two or three administrations per day. The dose may be increased or decreased, as appropriate, depending on age, pathologic conditions, and symptoms.

The timing of administration and administration period of the medicament of the present invention are not particularly limited, and these conditions can be determined, as appropriate. For example, the medicament of the present invention may be preventively administered before the onset of ophthalmologic disease caused by ocular angiogenesis. In addition, after the onset of ophthalmologic disease caused by ocular angiogenesis, the present medicament may also be administered for the purpose of treating the disease, ameliorating symptoms, or preventing deterioration of the symptoms. In the present invention, such an action to administer the medicament of the present invention to an individual after the onset of ophthalmologic disease is an aspect of treatment, even if the purpose thereof is prevention of deterioration of the symptoms.

As the medicament of the present invention, the compound represented by the above formula (I) or a physiologically acceptable salt thereof, or a hydrate thereof or a solvate thereof may be directly administered. In general, however, it is preferable to prepare a pharmaceutical composition comprising the above-described substance as an active ingredient and pharmacologically and pharmaceutically acceptable additives, and then, to administer the prepared pharmaceutical composition.

Examples of the pharmacologically and pharmaceutically acceptable additives that can be used herein may include excipients, disintegrators or adjuvants for the disintegrators, binders, lubricants, coating agents, dye, diluents, bases, resolvents or solubilizers, isotonizing agents, pH modifiers, stabilizers, propellants, and adhesives.

Examples of additives for the pharmaceutical composition, which is suitable for oral administration, may include: excipients such as glucose, lactose, D-mannitol, starch, or crystalline cellulose; disintegrators or adjuvants for the disintegrators, such as carboxymethylcellulose, starch, or carboxymethylcellulose calcium; binders such as hydroxypropylcellulose, hydroxypropylmethylcellulose, polyvinylpyrrolidone, or gelatin; lubricants such as magnesium stearate or talc; coating agents such as hydroxypropylmethylcellulose, saccharose, polyethylene glycol, or titanium oxide; and bases such as petrolatum, liquid paraffin, polyethylene glycol, gelatin, kaolin, glycerin, purified water, or hard fat.

Examples of additives for the pharmaceutical composition, which is suitable for injection or drip, may include: a resolvent or a solubilizer, which can constitute an aqueous injection, such as distilled water for injection, normal saline, and propylene glycol, or an injection to be dissolved before use; isotonizing agents such as glucose, sodium chloride, D-mannitol, or glycerin; and pH modifiers such as inorganic acid, organic acid, inorganic base, or organic base.

With regard to a pharmaceutical composition suitable for eye drops, an aqueous solvent such as sterilized purified water or normal saline, or a non-aqueous solvent including vegetable oil such as cottonseed oil, soybean oil, sesame oil or peanut oil is used, and the compound represented by the above formula (I) or a salt thereof is then dissolved or suspended in the aqueous or non-aqueous solvent, so as to prepare the pharmaceutical composition suitable for eye drops. In this operation, an isotonizing agent, a pH modifier, a thickener, a suspending agent, an emulsifier, a preservative and the like may be appropriately added to the mixture, as necessary. Examples of the isotonizing agent that can be used herein may include sodium chloride, boric acid, sodium nitrate, potassium nitrate, D-mannitol, and glucose. Examples of the pH modifier that can be used herein may include boric acid, anhydrous sodium sulfite, hydrochloric acid, citric acid, sodium citrate, acetic acid, potassium acetate, sodium carbonate, and borax. Examples of the thickener that can be used herein may include methylcellulose, hydroxypropylmethylcellulose, polyvinyl alcohol, sodium chondroitin sulfate, and polyvinylpyrrolidone. Examples of the suspending agent that can be used herein may include polysorbate 80, polyoxyethylene hydrogenated castor oil 60, and polyoxy castor oil. Examples of the emulsifier that can be used herein may include egg yolk lecithin and polysorbate 80. Examples of the preservative that can be used herein may include benzalkonium chloride, benzethonium chloride, chlorobutanol, phenylethyl alcohol, and ethyl 4-hydroxybenzoate.

The form of the medicament of the present invention is not particularly limited, and the present medicament can have various forms that are available to a person skilled in the art. As medicaments suitable for oral administration, tablets, capsules, powders, fine granules, granules and the like can be prepared using solid additives for pharmaceutical agents. In addition, using liquid additives for pharmaceutical agents, syrups and the like can be prepared. On the other hand, as medicaments suitable for parenteral administration, injections, infusions, eye drops, suppositories, transdermal absorption agents and the like can be prepared. Since a brain protective agent (drip) comprising, as an active ingredient, the above-described compound of the formula (I) has already been used in clinical sites (the general name "edaravone" and the commercial name "Radicut": produced and marketed by Mitsubishi Pharma Corporation), the aforementioned commercially available agent can be directly used as the medicament of the present invention.

The administration route of the medicament of the present invention is not particularly limited, and the present medicament can be orally or parenterally administered. The administration route in the case of parenteral administration is not particularly limited, either, and the present medicament can be injected into the vein or the artery, or it can also be administered in the form of eye drops.

The diseases that are the targets of the medicament of the present invention are ophthalmologic diseases caused by ocular angiogenesis, and are preferably ophthalmologic diseases caused by angiogenesis occurring in cornea, choroid or retina. Specific examples of the ophthalmologic diseases caused by ocular angiogenesis may include, but are not particularly limited to, retinopathy of prematurity, diabetic retinopathy, corneal neovascularization, wet age-related macular degeneration, neovascular glaucoma, choroidal neovascularization, neovascular maculopathy, branch retinal vein occlusion, central retinal vein occlusion, branch retinal artery occlusion, central retinal artery occlusion, and diabetic maculopathy. Among the above-described diseases, retinopathy of prematurity, corneal neovascularization, wet age-related macular degeneration, neovascular glaucoma, choroidal neovascularization, and neovascular maculopathy are preferable, and wet age-related macular degeneration or neovascular maculopathy is more preferable.

The medicament of the present invention has the action of a preventive agent for preventing ophthalmologic disease caused by ocular angiogenesis, and/or the action of a therapeutic agent for recovering ophthalmologic disease caused by ocular angiogenesis to a normal state.

EXAMPLES

Hereinafter, the present invention will be more specifically described in the following examples. However, these examples are not intended to limit the scope of the present invention.

Synthetic Example

Synthesis of 3-methyl-1-phenyl-2-pyrazolin-5-one (Hereinafter Referred to as "edaravone")

13.0 g of Ethyl acetoacetate and 10.8 g of phenylhydrazine were added into 50 ml of ethanol, and the obtained mixture was then stirred under reflux for 3 hours. Thereafter, the reaction solution was allowed to cool, and the precipitated crystals were then collected by filtration. The crystals were then recrystallized from ethanol to obtain 11.3 g of the title compound in the form of colorless crystals.

Yield: 67%

Melting point: 127.5° C. to 128.5° C.

Example 1

Using mouse models which were experimentally induced to have choroidal neovascularization (hereinafter referred to as "CNV") by laser irradiation (CNV models), the effectiveness of the medicament on the area of CNV was evaluated. In such CNV models, macrophages migrate as a result of provocation of inflammation by laser irradiation. Consequently, VEGF is generated, and new blood vessels are formed. Accordingly, the CNV models are considered to be experimental models demonstrating the effectiveness of a medicament on diseases associated with ocular angiogenesis.

A 10-fold dilution of a mixed anesthetic solution of ketamine and xylazine (7:1) was administered at a dose of 10 mL/kg into the femoral muscle of each mouse, and one eye was then irradiated with laser at 6 sites with equal intervals on the circumference of discus nervi optici (wave length: 647 nm, spot size: 50 μm, irradiation time: 100 msec, and laser output: 120 mW). Immediately after the laser irradiation, 3 mg/kg edaravone, 10 mg/kg edaravone, or 10 mL/kg normal saline was administered into the caudal vein of each mouse. Thereafter, fundus photography was carried out using a fundus camera. Fourteen days after the laser irradiation, a 10-fold dilution of Fluorescite (registered trademark) Injection Solution No. 1 was administered at a dose of 0.5 mL/kg into the caudal vein under the same anesthesia as described above, and fluorescein fundus photography was then carried out using a fundus camera. Fourteen days after the laser irradiation, after completion of the fluorescein fundus photography, 0.5 mL of FITC-dextran (20 mg/mL) was further administered into the caudal vein. After that, the mice were subjected to euthanasia by cervical dislocation, and their eye ball was then excised. The expression of CNV was evaluated by choroidal flat mount. Using a confocal laser scanning microscope, the CNV was photographed, and the area of CNV was then measured. FIG. 1A shows an image of CNV that has been photographed using the confocal microscope, and FIG. 1B is a graph showing the results of CNV area quantification. As shown in FIG. 1A and FIG. 1B, the CNV formation was inhibited in mice by administration of edaravone into the caudal vein thereof.

Example 2

Using CSC Complete Recombinant Medium, human retinal microvascular endothelial cells (HRMECs) were plated at a cell density of $2 \times 10^3$ cells/well on a 96-well plate. Twenty-four hours after plating, the medium was exchanged with a CSC medium containing 10% fetal bovine serum (FBS). Then, twenty-four hours after the medium exchange, edaravone was added in a final concentration of 1, 10 or 100 μM to an edaravone addition group. One hour after the addition of edaravone, to a vascular endothelial growth factor (VEGF) addition group, VEGF was added in a final concentration of 10 ng/mL. Twenty-four hours after the addition of VEGF, in order to remove the reagent and VEGF, the medium was exchanged again with a CSC medium containing 10% FBS. After completion of the medium exchange, cell counting kit-8 was added, and the absorbance at 450 nm was then measured (defined as "measurement value 1"). Three hours after the measurement of the absorbance, the second absorbance measurement was carried out (defined as "measurement value 2"). The measurement value 1 was subtracted from the measurement value 2, and the obtained value was then corrected, using a control group, to which VEGF had not been added, as 100%. The thus obtained value was defined as a growth rate. The cells were cultured under conditions of 37° C. and 5% $CO_2$, except for the operations. The measurement results are shown in FIG. 2. As shown in FIG. 2, the cell growth induced by VEGF was suppressed by the addition of edaravone.

The invention claimed is:

1. A method for treating an ophthalmologic disease caused by ocular angiogenesis, which comprises a step of administering to a human, an effective amount of a pyrazolone compound represented by the following formula (I), or a physiologically acceptable salt thereof, or a hydrate thereof or a solvate thereof:

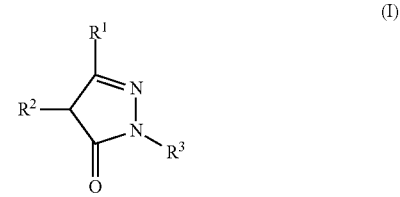

(I)

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl, or $C_{1-3}$ hydroxyalkyl, or $R^1$ and $R^2$ are combined with each other to represent $C_{3-5}$ alkylene, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, a halogen atom, trifluoromethyl, carboxyl, cyano, a hydroxyl group, nitro, amino, and acetamide.

2. The method according to claim 1, wherein the pyrazolone compound represented by the formula (I) is 3-methyl-1-phenyl-2-pyrazolin-5-one.

3. The method according to claim 1, wherein the ophthalmologic disease caused by ocular angiogenesis is an ophthalmologic disease caused by angiogenesis occurring in a cornea, choroid or retina.

4. The method according to claim 1, wherein the ophthalmologic disease caused by ocular angiogenesis is at least one selected from the group consisting of retinopathy of prematurity, diabetic retinopathy, corneal neovascularization, wet age-related macular degeneration, neovascular glaucoma, choroidal neovascularization, neovascular maculopathy, branch retinal vein occlusion, central retinal vein occlusion, branch retinal artery occlusion, central retinal artery occlusion, and diabetic maculopathy.

5. A method for treating wet age-related macular degeneration or neovascular maculopathy, which comprises a step of administering to a human an effective amount of 3-methyl-1-phenyl-2-pyrazolin-5-one.

6. A method for inhibiting ocular angiogenesis, which comprises a step of administering to a human an effective amount of a pyrazolone compound represented by the following formula (I), or a physiologically acceptable salt thereof, or a hydrate thereof or a solvate thereof:

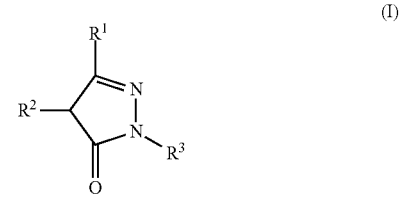

(I)

wherein $R^1$ represents a hydrogen atom, aryl, $C_{1-5}$ alkyl, or $C_{3-6}$ (total carbon number) alkoxycarbonylalkyl, $R^2$ represents a hydrogen atom, aryloxy, arylmercapto, $C_{1-5}$ alkyl, or $C_{1-3}$ hydroxyalkyl, or $R^1$ and $R^2$ are combined with each other to represent $C_{3-5}$ alkylene, and $R^3$ represents a hydrogen atom, $C_{1-5}$ alkyl, $C_{5-7}$ cycloalkyl, $C_{1-3}$ hydroxyalkyl, benzyl, naphthyl or phenyl, or phenyl substituted with the same or different 1 to 3 substituents selected from the group consisting of $C_{1-5}$ alkoxy, $C_{1-3}$ hydroxyalkyl, $C_{2-5}$ (total carbon number) alkoxycarbonyl, $C_{1-3}$ alkylmercapto, $C_{1-4}$ alkylamino, $C_{2-8}$ (total carbon number) dialkylamino, a halogen atom, trifluoromethyl, carboxyl, cyano, a hydroxyl group, nitro, amino, and acetamide.

7. The method according to claim 6, wherein the pyrazolone compound represented by the formula (I) is 3-methyl-1-phenyl-2-pyrazolin-5-one.

8. The method according to claim 6, wherein the ocular angiogenesis is angiogenesis occurring in a cornea, choroid or retina.

9. The method according to claim 6, wherein the ocular angiogenesis is inhibited by suppressing cell growth induced by a vascular endothelial growth factor (VEGF).

10. The method according to claim 3, wherein the pyrazolone compound represented by the formula (I) is 3-methyl-1-phenyl-2-pyrazolin-5-one.

11. The method according to claim 4, wherein the pyrazolone compound represented by the formula (I) is 3-methyl-1-phenyl-2-pyrazolin-5-one.

12. The method according to claim 8, wherein the pyrazolone compound represented by the formula (I) is 3-methyl-1-phenyl-2-pyrazolin-5-one.

13. The method according to claim 9, wherein the pyrazolone compound represented by the formula (I) is 3-methyl-1-phenyl-2-pyrazolin-5-one.

* * * * *